(12) United States Patent
Pappolla et al.

(10) Patent No.: US 6,274,615 B1
(45) Date of Patent: *Aug. 14, 2001

(54) METHOD FOR DELAYING THE ONSET OF ALHEIMER'S DISEASE AND FOR TREATMENT OR DELAYING THE ONSET OF OTHER AMYLOIDOSIS-RELATED DISEASES/DISORDERS

(75) Inventors: Miguel A. Pappolla, Mobile, AL (US); Blas Frangione, New York; Jorge Ghiso, Elmhurst, both of NY (US)

(73) Assignees: South Alabama Medical Science Foundation, Mobile, AL (US); New York University, New York City, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/276,171

(22) Filed: Mar. 25, 1999

Related U.S. Application Data (60) Provisional application No. 60/079,349, filed on Mar. 25, 1998.

(51) Int. Cl.⁷ .................................................. A61K 31/405
(52) U.S. Cl. ............................................................ 514/415
(58) Field of Search ..................................... 514/415, 879

(56) References Cited

U.S. PATENT DOCUMENTS

| | | | |
|---|---|---|---|
| 4,600,723 | 7/1986 | Short et al. | 514/416 |
| 4,665,086 | 5/1987 | Short et al. | 514/416 |
| 5,242,941 | 9/1993 | Lewy et al. | 514/416 |
| 5,707,652 * | 1/1998 | Lewy et al. | 424/457 |
| 5,958,964 * | 9/1998 | Pappolla | 514/415 |

OTHER PUBLICATIONS

Miguel Pappolla et al., "Melatonin Prevents Death of Neuroblastoma Cells Exposed to The Alzheimer Amyloid Peptide"; *The Journal of Neuroscience*, 17(5):1683–1690 (Mar. 1, 1997).

Russel Reiter et al., "Prophylactic Actions of Melatonin in Oxidative Neurotoxicity"; *Ann. N.Y. Acad. Sci.*, 825:70–78 (1997).

Arendt et al., "Some effects of jet–lag and their alleviationby melatonin", *Ergonomics* 30(9):1379–1393 (1987).

Bendheim et al., "Nearly ubiquitous tissue distribution of the scrapie agent precursor protein", *Neurol* 42:149–156(1992).

Bendheim et al., "Antibodies to a scrapie prion protein", *Nature* 310:418–421 (1984).

Benitez–King et al., "Calmodulin mediates melatonin cytoskeletal effects", *Experientia* 49(8):635–641 (1993).

Bolton et al., Isolation and structural studies of the intact Scrapie Agent Protein, *Arch Biochem Biophys* 258(2):579–590 (1987).

Cai et al., "Release of Excess Amyloid β Protein Precursor", *Science* 259:514–516 (1993).

DeArmond et al., "Indentification of Prion Amyloid Filaments in Scrapie–Infected Brain", *Cell* 41:221–235 (1985).

Dyrks et al., "Amyloidogenicity of βA4 and βA4–bearing Amyloid Protein Precursor Fragments by Metal–catalzed Oxidation", *J.Biol Chem* 267(25):18210–18217 (1992).

Ghetti et al., "Gerstmann–stäussler–Scheinker disease. II. Neurofibrillary tangles and plaques with PrP–amyloid coexist in an affected family", *Neurol* 39:1453–1461 (1989).

Glenner et al., "Alzheimer's Disease: Initial Report of the Purification and Characterization of a Novel Cerebrovascular Amyloid Protein", *Biochem Biophys Res Commun* 120(3):885–890 (1984).

Huerto–Delgadillo et al., "Effects of melatonin on microtubule assembly depend on hormone concentration: Role of melatonin as a calmodulin antagonist", *J Pineal Res* 17:55–62 (1994).

Kitamoto et al., "Amyloid Plaques in Creutzfeldt–Jakob Disease Stain with Prion Protein Antibodies", *Ann Neurol* 20:204–208 (1986).

Kitamoto et al., "A prion protein missense variant in kuru plaque cores in patients with Gerstmanm–Sträussler syndrome", *Neurol* 41:306–310 (1991).

LeBars et al., "PET and Plasma Pharmocokinetic Studies after Bolus Intravenous Adminstration of [$^{11}$C]Melatonin in Humans", *Nucl ed Biol* 18(3):357–361 (1991).

Mishima et al., "Morning bright light therapy for sleep and behavior disorders in elderly patients with dementia", *Acta Psychiatr Scand* 89:1–7 (1994).

Oesch et al., "A Cellular Gene Encodes Scrapie PrP 27–30 Protein", *Cell* 40:735–746 (1985).

Pappolla et al., "Immunohistochemical Evidence of Antioxidant Stress in Alzheimer's Disease", *Am J Pathol* 140(3):621–628 (1992).

Pappolla et al., "Neuropathology and Molecular Biology of Alzeheimer's Disease", in *Perspectives on Behavioral Medicine Alzeheimer's Disease*, Stein et al. Eds., Academic Press (San Diego), pp. 3–20 (1995).

Pappolla et al., "The Heat Shock/Oxidative Stress Connection: Relevance to Alzeheimer Disease", *Mol and Chem Neuropath* 28:21–34.

(List continued on next page.)

Primary Examiner—Kevin E. Weddington
(74) Attorney, Agent, or Firm—Browdy and Neimark (57) ABSTRACT

The present invention relates to a method of using melatonin to reduce, inhibit or reverse the formation of amyloid fibrils and amyloid or amyloid-like deposits. The present invention also relates to a method for delaying the onset of Alzheimer's Disease or other amyloidosis-related diseases/disorders or for treating such diseases/disorders by administering an effective amount of melatonin to a subject in need thereof.

12 Claims, 4 Drawing Sheets

OTHER PUBLICATIONS

Pappolla et al., "Disruption of β–Fibrillogensis by the Pineal Hormone Melatonin", *Soc for Neurosci Abstr* 23(1–2):1881 (1997).

Pappolla et al., "Melatonin Prevents Death of Neuroblastoma Cells Exposed to the Alzheimer Amyloid Peptide", *J Neurosci* 17(5):1683–1690 (1997).

Pappolla et al., "Inhibition of Alzeheimer β–Fibrillogensis by Melatonin", *J Biol Chem* 273(13):7185–7188 (1988).

Pierpaoli et al, "The pineal gland: A circadian or seasonal aging clock?", *Aging*3(2):99–101 (1991).

Pierpaoli et al., "The Pineal Control of Aging: The Effects of Melatonin and Pineal Grafting on the Survival of Older Mice", *Ann NY Acad Sci* 621:291–313 (1991).

Prusiner, "Molecular Biology of Prion Diseases", *Science* 252:1515–1522 (1991).

Puckett et al., "Genomic Structure of the Human Prion Protein Gene", *Am J Hum Genet* 49:320–329.

Reiter et al., "Antioxidant Capacity of Melatonin: A Novel Action Not Requiring a Receptor", *Neuroendoc Lett* 15(1–2):103–116 (1993).

Reiter, "ThePineal Gland and Melatonin in Relation to Aging: A Summary of the Theories and of the Data", *Exp Gerontol* 30(3/4):199–212 (1995).

Reiter et al., "Oxidative Toxicity in Models of Neurodeneration: Responses to Melatonin", *Rest Neurol Neurosci* 12(2–3):135–142 (1999).

Robakis et al., "Involvement of amyloid as a central step in the development of Alzeheimer's disease", *Neurobiol Aging.* 15 Suppl 2:S127–129 (1994).

Safar et al., "Molecular mass, biochemical composition, and physiocochemical behavior of the infectious form of the scrapie precursor protein monomer", *Proc Natl Acad Sci USA*; 87(16):6373–6377 (1990).

Selkoe, "Amyloid β–Protein and the Genetics of Alzeheimer's Disease",*J Biol Chem* 27(31):18295–18298 (1996).

Skene et al., "Daily variation in the concentration of melatonin and 5–methoxytryptophol in the human pineal gland: effect of age and Alzeheimer'disease", *Brain Research* 528:170–174 (1990).

Snyder et al., "Amyloid–β Aggregation in Mixtures od Amyloid with Different Chain Lengths", *Biophys J* 67:1216–1228 (1994).

Souétre et al., "Abnormal Melatonin Response to 5–Methoxypsoralen in Dementia", *Am J Psychiatry* 146(8)1037–1040 (1989).

Tagliavini et al., "Amyloid protein of Germann–Sträussler–Scheinker disease (Indiana kindred) is an 11 kd fragment of prion protein with an N–teerminal glycine at codon 58", *EMBO J* 10(3):513–519 91991).

Turk et al., "Purification and properties of the cellular and scrapie hamster prion proteins", *Eur J Biochem* 176:21–30 (1987).

van Renberg et al., "A new model for the pathophysiology of Alzeheimer's disease", *SAMJ* 87(9):1111–1115 (1999).

Weidemann et al., "Identification, Biogensis, and Localization of Precursors of Alzeheimer's Disease A4 Amyloid Protien",*Cell* 57:115–126 (1989).

Wisniewski et al., "Peptides Homologous to the Amyloid Protein of Alzeheimer's Disease Containing a Glutamine for Glutamine Acid Substitution Have Accerlerated Amyloid Fibril Formation", *Biophys Res Commun* 17(3):1247–1254c(1991).

Wisniewski et al., "Accerleration of Alzeheimer's Fibril Formation by Apolipoprotein E *In Vitro*", *Am J Pathol* 145(5):1030–1035 (1994).

* cited by examiner

| | Aβ | +NAT | +PBN | +Mel |
|---|---|---|---|---|
| α-helix | 2 | 1 | 2 | 3 |
| β-sheet | 52 | 54 | 49 | 33 |
| β-turn | 29 | 26 | 26 | 22 |
| random | 16 | 20 | 23 | 42 |

FIG. 1C

| | Aβ | +NAT | +PBN | +Mel |
|---|---|---|---|---|
| α-helix | 1 | 1 | 1 | 3 |
| β-sheet | 66 | 56 | 48 | 24 |
| β-turn | 26 | 23 | 23 | 18 |
| random | 7 | 19 | 27 | 55 |

| | Aβ | +NAT | +PBN | +Mel |
|---|---|---|---|---|
| α-helix | 2 | 3 | 2 | 4 |
| β-sheet | 89 | 85 | 80 | 65 |
| β-turn | 1 | 1 | 3 | 10 |
| random | 8 | 11 | 15 | 21 |

FIG. 1G

| | Aβ | +NAT | +PBN | +Mel |
|---|---|---|---|---|
| α-helix | 2 | 3 | 3 | 3 |
| β-sheet | 95 | 90 | 77 | 59 |
| β-turn | 2 | 3 | 4 | 10 |
| random | 1 | 4 | 16 | 28 |

METHOD FOR DELAYING THE ONSET OF ALHEIMER'S DISEASE AND FOR TREATMENT OR DELAYING THE ONSET OF OTHER AMYLOIDOSIS-RELATED DISEASES/DISORDERS

CROSS-REFERENCE TO RELATED APPLICATIONS

The present application claims the benefit of priority under 35 U.S.C. §119(e) from U.S. provisional application Ser. No. 60/079,349, filed Mar. 25, 1998, the entire content of which are hereby incorporated by reference.

GOVERNMENT LICENSE RIGHTS

The experiments performed in this application were supported by the National Institutes of Health, Grant Nos. AG11130, AG05891, AR02594, AG08992, and AG14363. The U.S. Government has a paid-up license in this invention and the right in limited circumstances to require the patent owner to license others on reasonable terms as provided by the terms of Grant Nos. AG11130, AG05891, AR02594, AG08992, and AG14363 awarded by the National Institutes of Health.

BACKGROUND OF THE INVENTION

1. Field of the Invention

The present invention relates to a method for delaying the onset of Alzheimer's Disease and for treating or delaying the onset of other amyloidosis-related diseases/disorders.

2. Description of the Related Art

It is estimated that ten percent of persons older than 65 years of age have mild to severe dementia. Alzheimer's Disease (AD) is the most common cause of chronic dementia with approximately two million people in the United States having the disease. Although once considered a condition of middle age, it is now known that the histopathologic lesions of Alzheimer's disease (i.e., neuritic amyloid plaques, neurofibrillary degeneration, and granulovascular neuronal degeneration) are also found in the brains of elderly people with dementia. The number of such lesions correlates with the degree of intellectual deterioration. This high prevalence, combined with the rate of growth of the elderly segment of the population, make dementia (and particularly AD) one of the most important current public health problems.

Deposition of cerebral amyloid is a primary neuropathologic marker of Alzheimer's disease. This amyloid is composed of a 40–42 amino acid peptide called the amyloid beta protein (Aβ) (Glenner et al., 1984). Amyloid deposits in AD are found mainly as components of senile plaques, and in the walls of cerebral and meningeal blood vessels (Robakis et al., 1994).

Molecular cloning showed that Aβ comprises a small region of a larger amyloid precursor protein (APP) (Robakis et al., 1987; Weidemann et al., 1989). Briefly, this is a type I integral membrane glycoprotein having a large extracytoplasmic portion, a smaller intracytoplasmic region, and a single transmembranous domain. APP undergoes extensive post-translational modifications (Pappolla et al., 1995; Robakis et al., 1994) prior to the secretion of its N-terminal portion (Sambamurti et al., 1992; Robakis et al., 1994). Physiologic processing of APP involves cleavage within the Aβ sequence by an unidentified enzyme, alpha-secretase (Anderson et al., 1991). Smaller quantities of APP molecules are cleaved at two other sites that could potentially produce amyloidogenic secreted or membrane bound APP (Robakis et al., 1994). Aβ is also produced during normal cellular metabolism (Haass et al., 1992; Shoji et al., 1992).

There is some controversy as to whether amyloid causes AD; however, three main lines of evidence have strengthened the amyloid hypothesis. The first piece of evidence is provided by the identification of several point mutations within the APP gene. These mutations segregate within a subgroup of patients afflicted with a familial form of the disorder and thus suggest a pathogenetic relationship between the APP gene and AD (Chartier-Harlin et al., 1991; Kennedy et al., 1993). Secondly, amyloid deposition temporally precedes the development of neurofibrillary changes (Pappolla et al., 1996) and this observation is also consistent with a link between amyloid and neuronal degeneration. Finally, it has been shown that Aβ is toxic to neurons (Yankner et al., 1990; Behl et al., 1992; Behl et al., 1994; Zhang et al., 1994), a finding that also strengthened the hypothesis that the amyloid peptide may contribute to the neuronal pathology in AD.

If amyloid deposition is a rate-limiting factor to produce AD, then all factors linked to the disease will either promote amyloid deposition or enhance the pathology that is provoked by amyloid. The likelihood of amyloid deposition is enhanced by trisonomy 21 (Down's syndrome) (Neve et al., 1988; Rumble et al., 1989), where there is an extra copy of the APP gene, by increased expression of APP, and by familial Alzheimer's Disease (FAD)-linked mutations (Van Broeckhoven et al., 1987; Chartier-Harlin et al., 1991; Goate et al., 1989; Goate et al., 1991; Murrell et al., 1991; Pericak-Vance et al., 1991; Schellenberg et al., 1992; Tanzi et al., 1992; Hendriks et al., 1992; Mullan et al., 1992). Some of these mutations are correlated with an increased total production of Aβ (Cai et al., 1993; Citron et al., 1992) or specific overproduction of the more fibrillogenic peptides (Wisniewski et al., 1991; Clements et al., 1993; Suzuki et al., 1994) or increased expression of factors that induce fibril formation (Ma et al., 1994; Wisniewski et al., 1994). The relationship between amyloid and the genetics of Alzheimer's Disease is well reviewed by Selkoe (1996). Collectively, these findings strongly favor the hypothesis that amyloid deposition is a critical element in the development of AD (Hardy 1992).

The finding that Aβ has neurotoxic properties has provided a possible connection between amyloid accumulation and neurodegeneration. Because of the close association between aging and AD and the similarities in the neuropathology of both conditions, oxidative stress has been proposed to play a role in the pathogenesis of AD lesions.

Several investigators demonstrated that oxygen free-radicals (OFRs) are related to the cytotoxic properties of Aβ (Behl, 1992; Behl, 1994; Harris et al., 1995; Butterfield et al., 1994; Goodman and Mattson, 1994). Such findings are important, since markers of oxidative injury are topographically associated with the neuropathologic lesions of AD (Pappolla et al., 1992; Furuta et al., 1995; Smith et al. 1995; Pappolla et al., 1996). Because of these observations, antioxidants have been proposed as potential therapeutic agents in AD (Mattson, 1994; Hensley et al., 1994; Pappolla et al., 1996).

Melatonin is a hormone which is synthesized and secreted primarily by the pineal gland and it acts both as a neurotransmitter and neurohormone. Being lipid soluble, it rapidly crosses the blood brain barrier and other tissues. Once released from the pineal gland, which is highly vascularized, melatonin enters the general circulation and the cerebrospinal fluid (CSF). Melatonin acts on the central and peripheral nervous system as well as on peripheral endocrine target tissues and has been implicated in many human disorders. Some disorders are known to be linked to chronobiologic abnormalities.

The in vivo levels of melatonin show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology. Melatonin has been administered in humans to re-synchronize circadian rhythms that are out of phase with local environmental cues, i.e., chronobiological therapy. For example, sleep/wake disorders associated with rapid crossing of time zones (jet lag), changes in work shifts, or those experienced by blind people can be treated with melatonin or melatonin analogs (U.S. Pat. Nos. 4,600,723; 4,665,086; and 5,242,941). Given orally in doses of 0.25–10 mg, melatonin has been used successfully to treat circadian disorders due to jet lag (Arendt et al., 1987; U.S. Pat. Nos. 4,600,723 and 5,242,941). Moreover, timed oral melatonin treatment apparently shifts the human circadian clock according to a phase-response curve (U.S. Pat. No. 5,242, 941).

Interestingly, melatonin also exhibits antioxidant properties (Reiter, 1995), but, in contrast to conventional antioxidants, this hormone has a proposed physiologic role in the aging process (Pierpaoli, 1991; Pierpaoli et al., 1991) and decreased secretion of melatonin with aging is documented (Iguchi et al., 1982; Dori et al., 1994). There are reports of more profound reductions of melatonin secretion in populations with dementia than in non-demented controls (Souetre et al., 1989; Mishima et al., 1994). It has been suggested that altered secretion levels of the hormone may partially reflect the loss of daily variation in the concentration of melatonin in the pineals of elderly individuals and AD patients (Skene et al., 1990). These facts regarding melatonin are in sharp contrast with conventional antioxidants which despite their reported cytoprotective characteristics have no comparable correlates with the pathophysiology of human aging.

The effects of melatonin are complex. In addition to its OFR scavenging properties, melatonin interacts with calmodulin (Benitez-King et al., 1993), microtubular components (Bentiez-King et al., 1993), and is reported to increase the activity of the intrinsic cellular antioxidant defenses (Huerto-Delgadillo et al., 1994). Melatonin, with its recently established antioxidant properties, was shown to be effective in preventing death of cultured neuroblastoma cells as well as oxidative damage and intracellular $Ca^{+2}$ increases induced by a cytotoxic fragment of amyloid β-protein (Pappolla et al., 1997). The use of melatonin for its cytoprotective effect in enhancing survivability of cells that have been subjected to the cytotoxic effects of amyloid β-protein as well as for treating patients afflicted with Alzheimer's Disease is disclosed in allowed U.S. patent application Ser. No. 08/801,301, which has not yet issued. Thus, the protective antioxidant effect of melatonin is only used therapeutically after the onset of Alzheimer's Disease.

Like amyloid fibrils, abnormal protein folding into β-sheet structures to form amyloid-like deposits is also widely believed to be the cause of prion-related encephalophathies, such as Creutzfeldt-Jakob disease (CJD) and Gerstmann-Straussler-Scheinker disease (GSS) in humans, scrapie in sheep and goats, and spongiform encephalopathy in cattle.

The cellular prion protein ($PrP^c$) is a sialoglycoprotein encoded by a gene that in humans is located on chromosome 20 (Oesch et al., 1985; Basler et al., 1968; Liao et al., 1986; Meyer et al., 1986; Sparkes et al., 1986; Bendheim et al., 1988 and Turk et al., 1988). The PrP gene is expressed in neural and non-neural tissues, the highest concentration of mRNA being in neurons (Chesebro et al., 1985; Kretzschmar et al., 1986; Brown et al., 1990; Cashman et al., 1990 and Bendheim et al., 1992).

The translation product of PrP gene consists of 253 amino acids in humans (Kretzschmar et al., 1986 and Pucket et al., 1991), 254 in hamster and mice or 256 amino acids in sheep and undergoes several post-translational modifications. In hamsters, a signal peptide of 22 amino acids is cleaved at the N-terminus, 23 amino acids are removed from the C-terminus on addition of a glycosyl phosphatidylinositol (GPI) anchor, and asparagine-linked oligosaccharides are attached to residues 181 and 197 in a loop formed by a disulfide bond (Turk et al., 1988; Hope et al., 1986; Stahl et al., 1987 and Safar et al., 1990).

In prion-related encephalophathies, $PrP^c$ is converted into an altered form designated $PrP^{Sc}$, that is distinguishable from $PrP^c$ in that $PrP^{Sc}$ (1) aggregates; (2) is proteinase K resistant in that only the N-terminal 67 amino acids are removed by proteinase K digestion under conditions in which $PrP^c$ is completely degraded; and (3) has an alteration in protein conformation from α-helical for $PrP^{Sc}$ to an altered form (Oesch et al., 1985; Bolton et al., 1982; McKinley et al., 1982; Bolton et al., 1984; Prusiner et al., 1984 and Bolton, 1987).

Several lines of evidence suggest that $PrP^{Sc}$ may be a key component of the transmissible agent responsible for prion-related encephalopathies (Prusiner, 1991) and it has been established that its protease-resistant core is the major structural protein of amyloid fibrils that accumulate intracerebrally in some of these conditions (Brendheim et al., 1984; DeArmond et al., 1985; Kitamoto et al., 1986; Robert et al., 1986; Ghetti et al., 1989; Tagliavini et al., 1991 and Kitamoto et al., 1991)

Citation of any document herein is not intended as an admission that such document is pertinent prior art, or considered material to the patentability of any claim or the present application. Any statement as to content or a date of any document is based on the information available to applicant at the time of filing and does not constitute an admission as to the correctness of such a statement.

SUMMARY OF THE INVENTION

The present invention provides a method for delaying the onset of Alzheimer's Disease or for treating or delaying the onset of other amyloidosis-related disease/disorders, which method includes administering an effective amount of melatonin to a subject in need thereof.

BRIEF DESCRIPTION OF THE DRAWINGS

FIGS. 1A–1H show circular dichroism of Aβ1-40 and Aβ1-42 alone or in the presence of melatonin. Spectral tracings for Aβ1-40 obtained at time 0 (FIG. 1A) and 24 hours (FIG. 1B) and for Aβ1-42 at time 0 (FIG. 1E) and 4 hours (FIG. 1F) are expressed in terms of mean residue ellipticity in units of deg $cm^2$ $dmol^{-1}$ after subtraction of buffer base-line spectra (including melatonin, NAT or PBN when indicated). The curves in FIGS. 1A, 1B, 1E, and 1F designate the spectra of Aβ alone (solid line), Aβ plus NAT (short dashes), Aβ plus PBN (long dashes), or Aβ plus melatonin (short and long dashes). The corresponding percentages of the different secondary structure motifs are shown for Aβ1-40 at time 0 in (FIG. 1C) and 24 hours (FIG. 1D) and for Aβ1-42 at time 0 (FIG. 1G) and 4 hours (FIG. 1H). An average of 40 scans/independent experimental condition was obtained. An independent experiment yielded qualitatively similar data.

FIGS. 2A–2D show electron micrographs of Aβ1-40 fibril formation in the presence or the absence of melatonin. Aβ1-40 was incubated for 48 hours either alone (FIG. 2A) or with NAT (FIG. 2B), PBN (FIG. 2C), or melatonin (FIG. 2D). Bar is 200 nm. Well formed amyloid fibrils are easily recognized in FIGS. 2A–2C. Fibrils were not formed in FIG. 2D. EM grids were extensively and carefully examined, and a negative result was only documented when fibrils were totally absent from the grids.

In FIG. 3B, the incubation time was 6 hrs. at a melatonin concentration of 100 μm. Well formed amyloid fibrils are easily recognized in FIG. 3A, but not in FIG. 3B.

DETAILED DESCRIPTION OF THE INVENTION

The present invention is based on the discovery that melatonin, a natural hormone of the pineal gland, interacts with amyloid β-protein (Aβ), and inhibits the progressive formation of β-sheets and amyloid fibrils. This discovery of the anti-fibrillogenic property of melatonin led to the development of the present method for delaying the onset of Alzheimer's Disease or for treating or delaying the onset of other amyloidosis-related diseases/disorders.

According to the method of the present invention, an effective amount of melatonin is administered to a subject in need thereof to reduce, inhibit or reverse the formation of fibrils or amyloid or amyloid-like deposits. While the present method is preferably directed to reducing, inhibiting or reversing the formation of fibrils in particular, it is also generally applicable to the formation of any type of amyloid or amyloid-like deposits whether fibrillar or nonfibrillar in structure.

As used herein, "amyloid β-protein" or "Aβ" refers to any one of the 40–42 amino acid residue peptides, i.e., Aβ1-40 and Aβ1-42, or mixtures thereof, that make up the cerebral amyloid which is the primary neuropathologic marker of Alzheimer's Disease (see Glenner et al., 1984, for the amino acid sequence of Aβ).

The term "amyloid or amyloid-like deposits" is meant to include amyloid fibrils as well as other amyloid or amyloid-like deposits, fibrillar or nonfibrillar in structure, which are recognized in the art as being amyloid or amyloid-like, such as deposits in senile cardiac amyloidosis, prion-related encephalopathies, and amylin in the kidney or pancreas of diabetic patients, etc. It is also intended to include pre-amyloid deposits, which unlike amyloid deposits, do not stain with Congo Red.

The term "melatonin," as used herein, preferably refers to the compound N-[2-(5-methoxy-1H-indol-3-yl) ethyl] acetamide, which is also known as N-acetyl-5-methoxy tryptamine, shown by the chemical structure below, where $R^2$, $R^3$, $R^4$, $R^6$, and $R^7$ are hydrogen, $R^5$ is methoxy and $R^1$ is methyl.

However, it is also intended that the term "melatonin" include analogs which have anti-fibrillogenic activity, such as those analogs having an alkoxy group at position 5 of the indolamine nucleus of melatonin. Such analogs have the chemical structure above, where $R^1$ is alkyl, $R^5$ is alkoxy, and $R^2$, $R^3$, $R^4$, $R^6$, and $R^7$ are independently selected from the group consisting of hydrogen, unsubstituted alkyl groups, substituted alkyl groups, unsubstituted aryl groups, substituted aryl groups, alkoxy groups, substituted or unsubstituted amino groups, thiol groups, alkylthiol groups arylthiol groups, and the like. Preferably, $R^2$ and $R^3$ are hydrogen. Preferred substituents are those which do not significantly affect the antifibrillogenic properties of melatonin. Although melatonin passes easily across the blood-brain barrier, melatonin analogs may show a reduced ability to cross the blood-brain barrier. For melatonin analogs that show a reduced ability to cross the blood-brain barrier, other suitable substituents are those which enhance brain penetration, such as a covalently bonded lipophilic moiety. These substituents can be present on any atom of the indole nucleus which has an available hydrogen. The mode of attachment of the lipophilic moiety is not critical, and can be effected by a carbon—carbon, carbon-oxygen, carbon-nitrogen, or carbon-sulfur bond. To maximize the lipophilicity of the resulting compound, however, it is preferred that attachment be effected so as to minimize polarity. Consequently, it is preferred that the lipophilic moiety be attached via a carbon-carbon bond. The lipophilic moiety can be a hydrocarbon, such as an alkyl having from 5 to 20 carbons. These alkyls can be unsubstituted, such as hexyl or dodecyl, or substituted, such as with an aryl moiety, as in the case where the substituted alkyl is a benzyl or a phenylethyl group. Alternatively, the lipophilic moiety can be substituted or unsubstituted homocyclic rings, such as phenyl groups or a tolyl groups, homocyclic ring systems, or heterocyclic rings, heterocyclic ring systems, or multicyclic lipophilic "cage" moieties, such as adamantane.

The subject to which melatonin is administered for delaying the onset of Alzheimer's Disease or other amyloidosis-related diseases/disorders is preferably an individual that has a predisposition, which may be genetic, to such diseases/disorders. These diseases/disorders include, but are not limited to, an individual having Down's syndrome, familial Alzheimer's Disease (FAD)-linked mutations, high copy number of the Apo-E4 allele, and mutations correlated with an increased total production of Aβ or specific overproduction of more fibrillogenic peptides, or increased expression of factors that induce fibril formation. Another notable predisposition is age. Because advanced age is a predisposition, it may be of benefit to administer melatonin to all individuals over the age of 50 to 55 who do not have Alzheimer's Disease. As melatonin has been used to treat mild conditions of circadian rhythm disruption, such as jet lag, and has also been tested in human subjects at very high doses, i.e., 1 g/day, without any clinically significant toxicity (Nordlund et al., 1977), it is quite safe. Accordingly, melatonin, which lacks toxicity and crosses the blood-brain barrier with ease (Tan et al., 1993) can be administered as a prophylactic to subjects in need thereof who are predisposed to amyloidosis-related diseases/disorders, such as Alzheimer's Disease, to delay the onset of such diseases/disorders.

In treating subjects in need thereof who are already afflicted with an amyloidosis-related disease/disorder other than Alzheimer's Disease, such as prion-related encephalopathies, senile cardiac amyloidosis, etc., the method according to the present invention can inhibit or reduce the formation of fibrils or amyloid or amyloid-like deposits or even reverse the formation (dissolution) of formed fibrils or amyloid or amyloid-like deposits. Examples of prion-related encephalopathies include Creutzfeldt-Jakob Disease (CJD), Gerstmann-Straussler-Scheinker disease (GSS) in humans, scrapie in sheep and goats, and spongiform encephalopathy in cattle. While the subject in need thereof to be administered melatonin is preferably human, the subject can also be other mammalian species which develop amyloidosis-related diseases/disorders.

For in vivo administration, the dosage is between about 20 mg to about 1500 mg of melatonin. Intravenous and oral administration of melatonin to treat circadian rhythm disorders usually involve pharmacological doses, so-called because they produce concentrations of melatonin that are up to several hundred times normal. While doses of melatonin in the range of 2 mg to gram quantities are considered pharmacological and not physiological, melatonin has been found to be remarkably non-toxic even in large doses. The dosage of melatonin used in the method according to the present invention is considerably higher, by at least several fold, than the dosage indicated for jet lag and other chronobiological disorders. The administrated dosage of melatonin is preferably in the range of about 50 to 1500 mg, more preferably in the ranges of about 50 to 500 mg or 100 to 500 mg.

The optimization of prophylactic or therapeutic efficacy in administering melatonin according to the method of the present invention, which optimization includes dosage, formulation for delivery (i.e., sustained release), administration schedule (i.e., at night or at intervals), can be determined by those of skill in the art with routine experimentation using conventional practices. For instance, it remains to be determined if it is more beneficial and efficacious to achieve a steady state serum concentration of melatonin in the subject or to achieve serum concentrations in the subject that reproduce the endogenous natural circadian rhythmicity. Those of skill in the art would recognize that if there are any undesirable side effects observed with maintaining a constant or nearly constant steady state serum concentration of melatonin, then an administration schedule which allows for reproducing of the subject's natural endogenous rhythmicity of serum melatonin levels can be used.

It will also be appreciated that the actual preferred amount of melatonin to be administered according to the present invention will vary according to the particular form of melatonin (for example, melatonin or an analog thereof), the particular composition formulated, and the mode of administration. Many factors that may modify the action of the melatonin can be taken into account by those skilled in the art e.g., body weight, sex, diet, time of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

Suitable routes of administration include systemic administration (because the melatonin will cross the blood-brain barrier). Systemic administration includes parenteral and oral administration, for example, as discussed in further detail below.

Melatonin may be administered alone or in combination with compatible pharmaceutically-acceptable carriers, excipients, diluents or auxiliary agents as a composition. The diluent, carrier, excipient or auxiliary agent should be selected so that they do not diminish the prophylactic or therapeutic effects of the melatonin as used in the present invention.

The compositions may be made up in any suitable form appropriate for the desired use; e.g., oral, parenteral, or topical administration. Suitable dosage forms for oral use include tablets, dispersible powers, granules, capsules, suspensions, syrups, elixirs, and skin patches. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

Having now generally described the invention, the same will be more readily understood through reference to the following example which is provided by way of illustration and is not intended to be limiting of the present invention.

EXAMPLE

Amyloid β protein (Aβ) plays a central role in the progressive neurodegeneration observed in Alzheimer's disease. Important pathologic properties of this protein, such as neurotoxicity and resistance to proteolytic degradation, depend on the ability of Aβ to form β-sheet structures or amyloid fibrils. The present example demonstrate that melatonin, a hormone recently found to protect neurons against Aβ toxicity, interacts with Aβ1-40 and Aβ1-42 and inhibits the progressive formation of β-sheets and amyloid fibrils. These interactions between melatonin and the amyloid peptides were demonstrated by circular dichroism and electron microscopy for Aβ1-40 and Aβ1-42 and by nuclear magnetic resonance spectroscopy for Aβ1-40. Inhibition of β-sheets and fibrils could not be accomplished in control experiments when a free radical scavenger or a melatonin analog were substituted for melatonin under otherwise identical conditions. The Materials and Methods used in this Example and the results obtained are presented below.

Materials and Methods

Circular Dichroism Spectroscopy

Peptides Aβ1-40 and Aβ1-42 were synthesized in the W. M. Keck Foundation (Yale University, Conn.), and their purity was evaluated by amino acid sequence and laser description mass spectrometry as described (Soto et al., 1996). Aliquots of Aβ1-40 and Aβ1-42 at a concentration of 250 μM in 5 mM Tris-HCl, pH 7.4, were incubated at room temperature alone or with 100 μM of either melatonin or the melatonin analog 5-hydroxy-N-acetyl-tryptamine (NAT) (Sigma Chemical Company, St. Louis, Mo.) or N-t-butyl-α-phenylnitrone (PBN) (Sigma), a powerful free radical scavenger structurally unrelated to melatonin. Because of the antioxidant properties of melatonin (Reiter et al., 1993) and because oxidative conditions may promote fibril formation (Snyder et al., 1994; Dyrks et al., 1992), NAT and PBN were specifically selected both as controls for the method and to discount for possible "nonspecific" antioxidant effects of melatonin in the phenomenon described here.

Spectra in the far ultraviolet light (190–250 nm) were recorded at various time intervals with a Jasco-720 spectropolarimeter as described (Soto et al., 1996) using a cell path of 0.01 cm. Experiments with Aβ1-42 necessitated shorter incubation times due to the more fibrillogenic properties and faster aggregation exhibited by the longer peptide. 40 scans/experimental condition were obtained at 0.2 nm intervals over the wavelength range 190–250 nm. The data were analyzed by the Lincomb algorithm (Perczel et al., 1992) to obtain the percentages of the different secondary structure motifs.

Electron Microscopy

To determine whether melatonin displayed inhibitory effects on amyloid fibril formation, transmission electron microscopy was performed following a standard method previously described (Pappolla et al., 1990) using a Phillipa CM100 microscope and Formvar-coated nickel grids. Aβ1-40 was incubated at the same concentrations as noted for the CD and NMR experiments in the presence or absence of melatonin, and fibril formation was monitored at 0, 12, 24, 26, and 48 h in three independent experiments. Additional controls containing Aβ plus NAT and Aβ plus PBN were incubated in parallel for 48 h. To determine the minimal inhibitory concentration of melatonin on fibril formation, experiments were preformed in which several melatonin concentrations (1 nM, 10 nM, 1 μM, 100 μM, and 200 μM) were added to tubes containing 250 μM Aβ1-40, incubated for 48 h, and then examined.

For the more amyloidogenic Aβ1-42, experiments were preformed at the same peptide concentration (250 μM) in the presence or absence of melatonin at various concentrations (100 nM, 1 μM, 10 μM, 100 μM, and 200 μM). The formation of amyloid fibrils was monitored at 0, 2, and 6 h.

Nuclear Magnetic Resonance Spectroscopy

To further explore structural changes of Aβ by melatonin, one-dimensional $^1$H NMR spectroscopic studies on Aβ1-40 were performed. The NMR approach has the distinct advantage of being able to specifically locate the amino acid side chains that bind to a particular ligand (Wemmer et al., 1994). The solution conditions for the NMR and CD studies were similar, except that deuterated water ($D_2O$) in phosphate buffer was used in the NMR study. All $^1$H NMR spectra were obtained at 600 MHz using a Varian UnityPlus-600 spectrometer, and the data were processed using the FELIX program (version 95.0, Biosym, Inc.). The NMR solutions were prepared in $D_2O$ (0.6 ml) with sodium phosphate buffer (5 mM, pH 7.5), perdeuterated $Na_2EDTA$ (0.5 mM), $NaN_3$ (0.05 mM), and 3-(trimethylsilyl) propionate-2,2,3,3-$d_4$ (0.05 mM), the last of which serves as a internal chemical shift reference at 0 ppm. The NMR measurements were performed at 10° C. and the residual proton absorption of $D_2O$ was suppressed by low power irradiation during the recycle delay. For all spectra, 128 scans were required with a total recycle delay of 4.2 s, which included an acquisition time and recycle delay of 2.2 and 2.0 s, respectively. The digital resolution of the acquired data was 0.24 Hz/pt, which was reduced to 0.12 Hz/pt by zero-filling the data once before processing. To further improve the resolution, before Fourier transformation spectra were multiplied by a Lorentzian-to-Gaussian weighting factor. This experiment was duplicated on two different days.

RESULTS

Circular Dichroism Studies

Figure 1A:
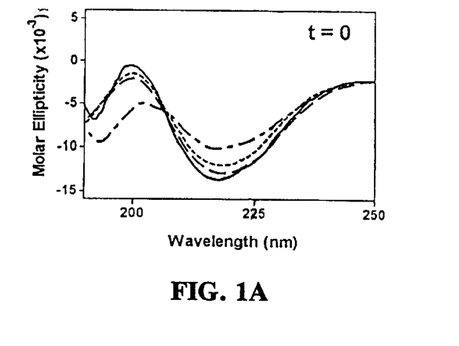
Figure 1B:
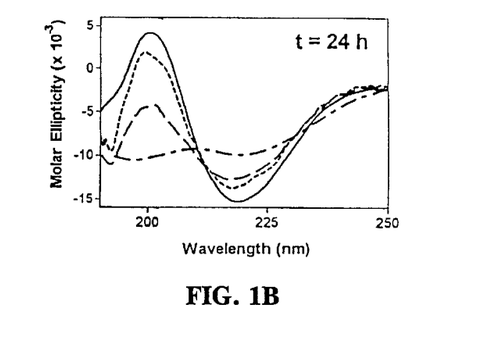
Figure 1C:
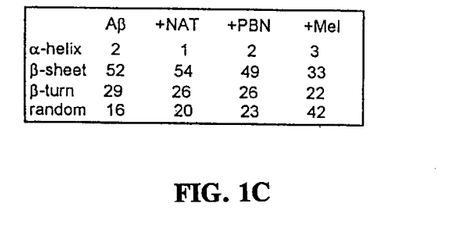
Figure 1D:
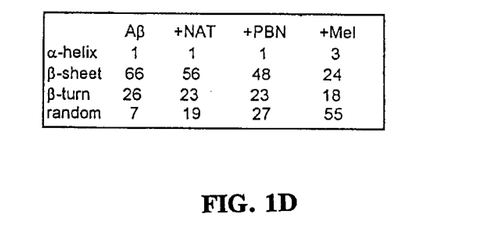
Figure 1E:
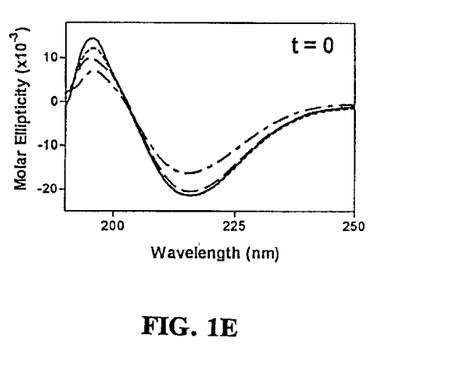
Figure 1F:
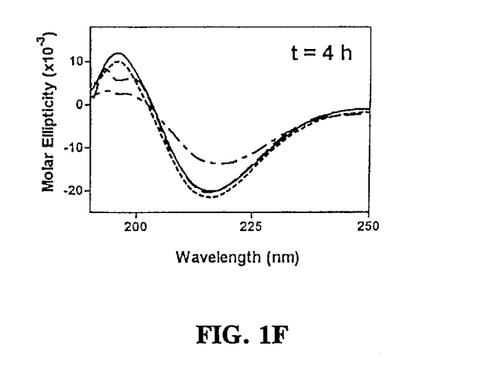
Figure 1G:
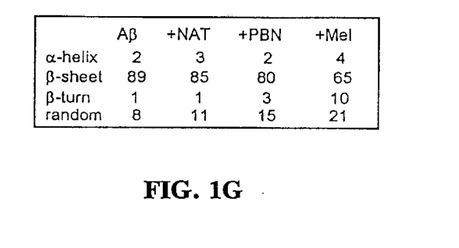
Figure 1H:
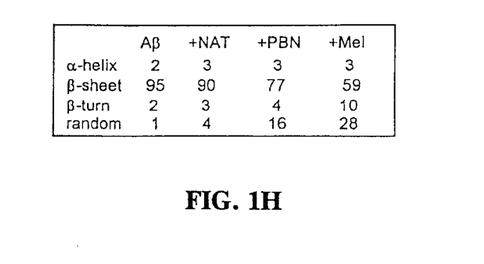

As expected, the content in β-sheet conformation of Aβ1-40 incubated alone increased over time from 52% at time 0 to 66% after 24 h at 37° C. (FIGS. 1A–1D). These results are in qualitative agreement with previous work (Terzi et al., 1995). The relative proportion of the structures was dramatically changed by addition of melatonin to sister tubes. At time 0, there was an immediate increase of the random conformation, whereas the original β-sheet content markedly diminished (FIGS. 1A and 1C). This effect was not observed with NAT or PBN. The amount of β-sheet structures for Aβ1-40 plus melatonin decreased over time, reaching 24% after 24 h of incubation (FIGS. 1B and 1D). At 24 h, no structural changes were again detected in control experiments with the melatonin analog NAT, and only small effects were observed with PBN. Experiments with the more amyloidogenic Aβ1-42 showed qualitatively similar results (FIGS. 1E–1H). Melatonin caused an immediate reduction in the amount of β-sheet structures at time 0 from 89 to 65% (FIGS. 1E and 1G). This percentage continued to decrease to 59% after 4 h of incubation (FIGS. 1F and 1H). As observed with Aβ1-40, such striking structural changes were not elicited in parallel control preparations containing Aβ1-42 plus NAT or PBN.

Electron Microscopy Studies

Figure 2A:
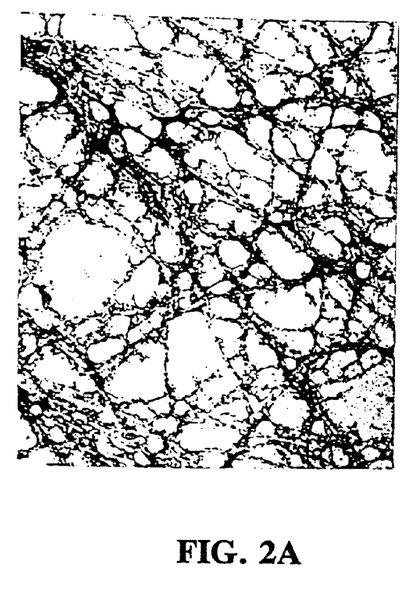
Figure 2B:
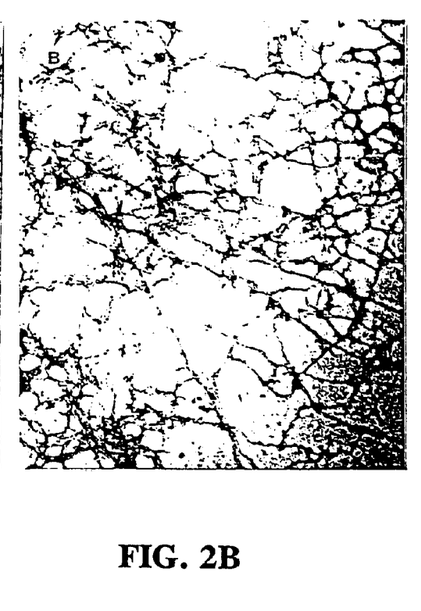
Figure 2C:
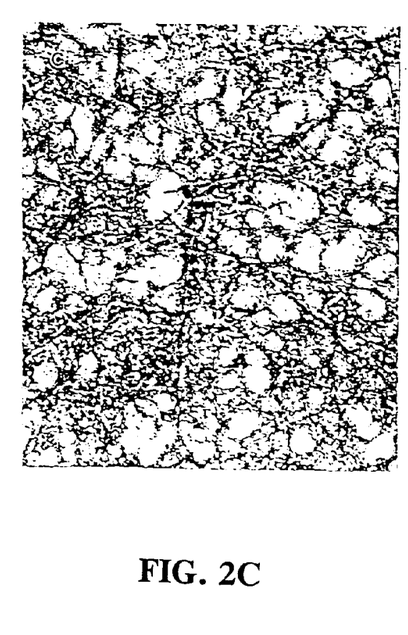
Figure 2D:
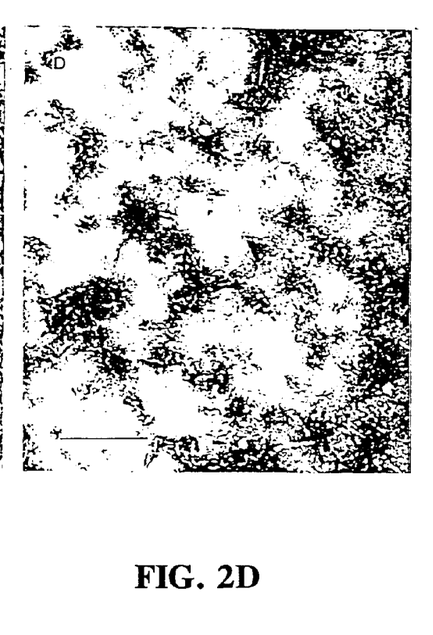

Results of the ultrastructural studies reflected the conformational changes and supported the hypothesis that formation of β-sheet structures precedes fibrillogenesis (Soto et al., 1995; Jarrett et al., 1993). In three independent experiments, fibrils were abundant in the tubes containing Aβ1-40 alone incubated for 36 h. In contrast, no fibrils were detected for solutions of Aβ1-40 plus melatonin incubated for up to 48 h (FIG. 2C). Notably, fibrils were abundant and easily identifiable in the tubes incubated for 48 h containing Aβ alone, Aβ plus NAT, or Aβ plus PBN, but not in the tubes containing Aβ plus melatonin. Such a contrasting finding suggests that the methoxy group at position 5 of the indolamine nucleus of melatonin confers relative structural specificity to the observed phenomena.

Fibril formation was inhibited in all tubes containing Aβ1-40 plus melatonin at concentrations above 10 μM. To substantiate the negative results obtained with PBN, three different concentrations of this scavenger (10, 100, and 200 μM) were added to tubes containing Aβ1-40, incubated for 48 h, and then examined. Fibrils were abundant in all these tubes. In contrast, only amorphous material was again identified in control sister tubes containing 250 µM Aβ1-40 plus 100 µM melatonin.

Figure 3A:
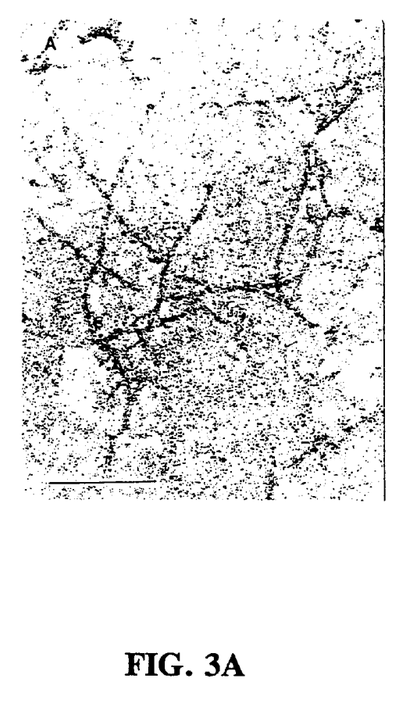
FIGS. 3A and 3B show electron micrographs of Aβ1-42 in the presence (FIG. 1B) or absence (FIG. 1A) of melatonin. Aβ1-42 was either incubated alone or with melatonin, as described in the materials and methods section of the Example.
Figure 3B:
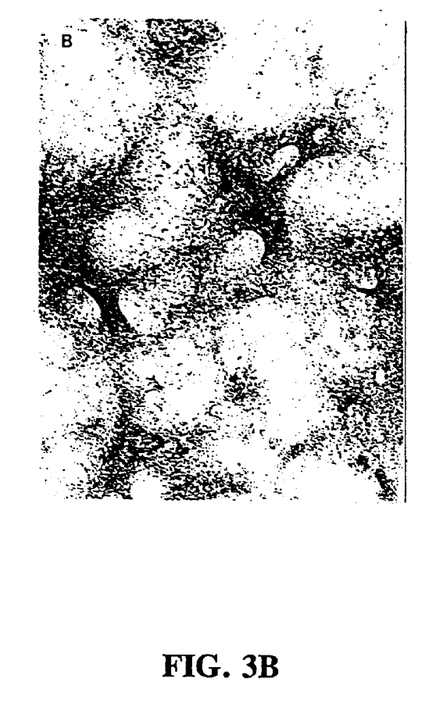

In the experiments with Aβ1-42, fibrils were identified in the tubes containing the peptide alone incubated after 2 and 6 h (no fibrils were seen at time 0). In contrast, only amorphous material was identified in the tubes containing Aβ1-42 plus melatonin at these time points (FIG. 3B). All the concentrations of melatonin used in the experiments with Aβ1-42, (as described in the Materials and Methods section above) were effective to inhibit fibril formation.

Nuclear Magnetic Resonance Spectroscopy

Figure 4:
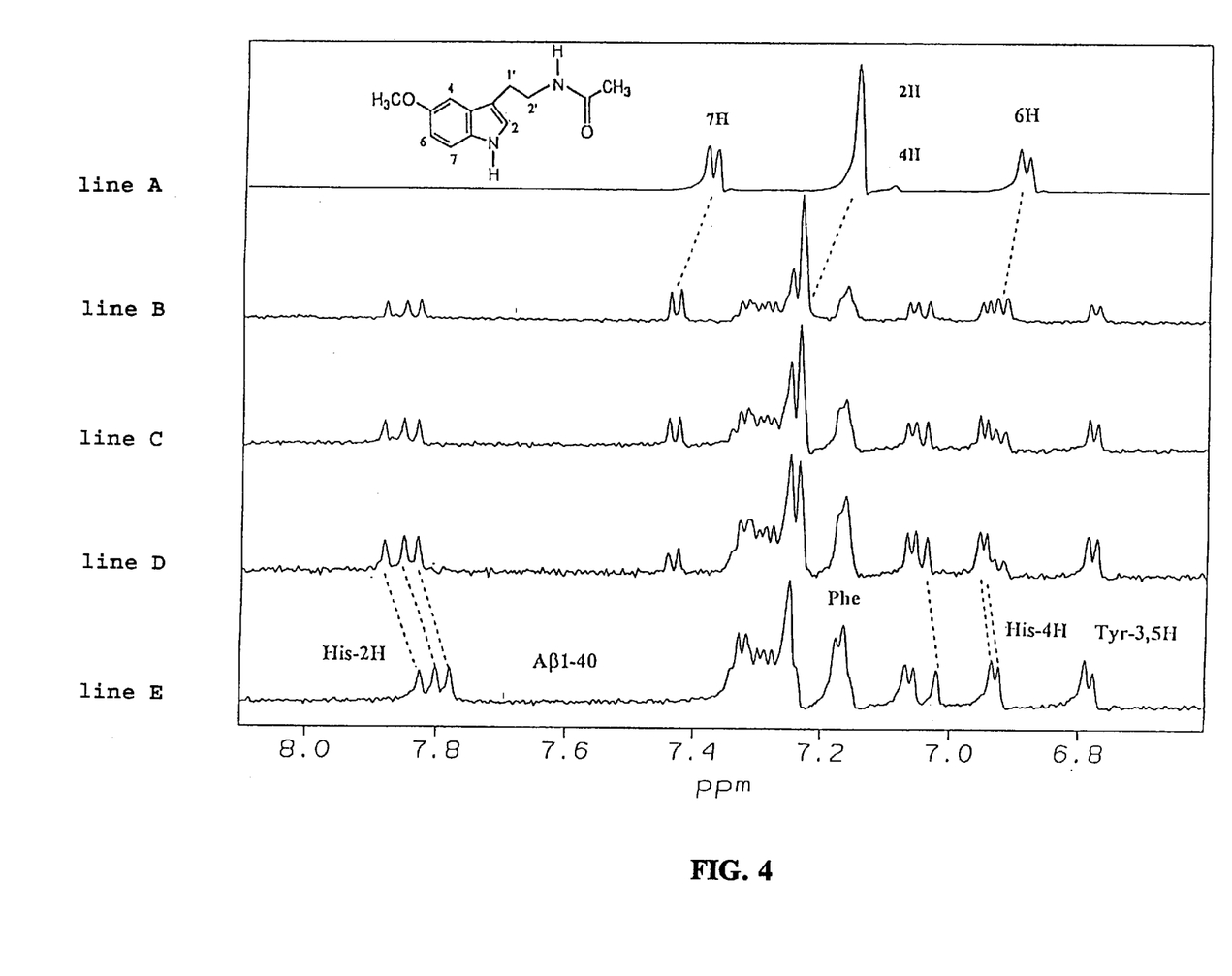
FIG. 4 is a single comparative figure showing downfield $^1$H-NMR spectral region (600 MHz) of 6.0 mM melatonin, with its chemical structure provided (Line A), and 0.25 mM Aβ1-40 peptide (Line E). The spectra in Lines B, C and D contain 0.25 mM Aβ1-40 plus 0.3, 0.2 and 0.1 mM melatonin, respectively. Assignments for the aromatic signals of melatonin and the Aβ1-40 peptide are shown, and those resonances exhibiting changes in shifts are connected by dotted lines. A duplicate independent experiment showed virtually identical results.

Shown in FIGS. 4A–4E are the downfield spectral regions for the Aβ1-40 peptide (FIG. 4E), melatonin (FIG. 4A) and the Aβ1-40 with 1.2, 0.8, and 0.4 molar equivalents of melatonin (FIGS. 4B–4D respectively). The three well resolved His-2H and His-4H signals are consistent with the Aβ1-40 peptide being partly folded into an ordered structure, which according to the CD studies should be β-sheet and random coil. If only random coil structure were present, then degenerated signals should be present for $His^6$, $His^{13}$ and $His^{14}$ (Zagorski et al., 1992).

The NMR spectra of the mixtures of melatonin and Aβ1-40 show changes in chemical shifts indicative of binding and local conformational changes. The His-2H and His-4H signals shift downfield 0.05 and 0.02 ppm, respectively, whereas the aromatic peaks of melatonin also shift downfield (FIG. 4A). In addition, careful analysis of the upfield spectral region (spectra not shown) revealed downfield shifts for the Asp $\beta CH_2$ groups (Table 1).

TABLE 1

Titration Studies* of Aβ(1-40) Peptide with Melatonin

| | Chemical shift | Bound chemical shift[a] ppm |
|---|---|---|
| Melatonin[b] | | |
| 3H | 7.15 | 0.09 |
| 4H | 7.15 | 0.09 |
| 6H | 6.89 | 0.03 |
| 7H | 7.38 | 0.05 |
| 1'-$CH_2$ | 2.92 | 0.04 |
| 2'-$CH_2$ | 3.48 | 0.01 |
| $CH_3$-N-acetyl | 1.91 | −0.01 |
| $CH_{3\text{-methoxyl}}$ | 3.87 | 0.03 |
| Aβ(1-40)[c] | | |
| His-4H | 6.92 | 0.02 |
| | 6.94 | 0.02 |
| | 7.01 | 0.02 |
| His-2H | 7.78 | 0.05 |
| | 7.80 | 0.05 |
| | 7.88 | 0.05 |
| Asp-$\beta CH_2$ | 2.84–2.77 | 2.87–2.80 |
| | 2.70–2.67 | 2.72–2.89 |

*All solutions contained 5 mM sodium phosphate buffer in $D_2O$, pH 7.5, at 10° C. with the chemical shifts referenced to internal 3-(trimethylsilyl) propionate-2,2,3,3-$d_4$.
[a]Obtained by subtracting the chemical shift of melatonin and the Aβ(1-40) peptide with the present data, we are unable to assign the 2H and 4H signals specifically to $His^6$, $His^{13}$, and $His^{14}$.
[b]Assignments for 5 mM melatonin.
[c]Because the $\beta CH_2$s for $Asp^1$, $Asp^7$, and $Asp^{23}$ are not resolvable by $^1H$ NMR, chemical shift ranges are presented.

Control NMR experiments with NAT showed only minor chemical shift perturbations (±0.01 ppm), suggesting a specificity for the interaction of melatonin with Aβ. The lack of any line broadening or separate peaks for the bound and free states indicates that the binding is in the fast exchange limit (Wemmer et al., 1994). The downfield shifts can be interpreted in terms of ringcurrent shift contributions, with the shifted hydrogens becoming located in the planes of the melatonin and His aromatic ring (Perkins et al., 1982). A remarkable feature is the identical shift seen for each of the three His residues. This result together with the observed non-linearity of the shifts with varied melatonin concentrations suggests that the binding is not localized to a particular His site on Aβ. Instead, the chemical shift changes are consistent with a residue-specific interaction between melatonin and any of the three His and Asp residues of Aβ.

Discussion

The results in this example clearly indicate that, under the conditions tested, melatonin modifies the secondary structure of the Aβ peptide and inhibits the formation of amyloid fibrils. The newly found anti-amyloidogenic properties of melatonin are very rare for endogenous substances. Because of the relationship between oxidative stress and AD and the recently established antioxidant properties of this hormone, it was initially thought that the neuroprotective actions of melatonin were mostly due to its intracellular antioxidant effects (Pappolla et al., 1990). However, the results presented here suggest that the anti-amyloidogenic properties are dependent on structural interactions of the hormone with Aβ rather than on antioxidant properties exclusively. The His and Asp residues play important roles in β-amyloid fibril production and stability. Many physiological constituents such as transthyretin and zinc can prevent or promote aggregation by their affinities for the His residues of Aβ (Bush et al., 1994; Schwarzman et al., 1994). Additionally, imidazole-carboxylate salt bridges between the side chains of the His and the Asp residues are critical to the formation of the amyloid β-sheet structures (Kirchner et al., 1987; Fraser et al., 1994; Fraser et al., 1991; Huang et al., 1997). More significantly, disruption of these salt bridges promotes fibril dissolution (Lee et al., 1995). One possibility is that melatonin promotes the β-sheet to random coil conversion by disruption of the $His^+$-$Asp^-$ salt bridges. Alternatively, the described effects may result from a unique combination of structural and antioxidant features of this molecule. The antioxidant properties of melatonin may provide additional cytoprotection at the intracellular level (Pappolla et al., 1997).

The ratio of melatonin: Aβ used in these studies is within physiologic range, because the concentration of both substances in the brain are normally around 1:1 during youth (both substances are at comparable picomolar concentrations in brain tissue during the dark phase of the cycle; Johnson-Wood et al., 1997; Pang et al., 1974). However, limitations of the methods employed required concentrations of melatonin and Aβ that deviate from actual physiological conditions.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Anderson et al., *Neurosci. Lett.* 128:126–129 (1991)
Arendt et al., *Ergonomics* 30:1379–1393 (1987)
Basler et al. (1986)
Behl et al., *Biochem. Biophys. Res. Commun.* 186:944–950 (1992)
Behl et al., *Brain Res.* 645:253–264 (1994)
Behl et al., *Cell* 77:817–827
Bendheim et al., *J. Infect. Dis* 158:1198–1208 (1988)
Bendheim et al., *Neurology* 42:149–156 (1992)
Benitez-King et al., *Experientia* 49(8):635–641 (1993)
Bolton et al., *Arch. Biochem. Biophys.* 258:1515–22 (1987)
Bolton et al., *Biochemistry* 23:5898–5905 (1984)
Bolton et al., *Science* 218:1309–1311 (1982)
Brendheim et al., *Nature* 310:418–421 (1984)
Brown et al., *Acta Neuropathol.* 80:1–6 (1990)
Bush et al., *J. Biol. Chem.* 269:12152–12158 (1994)
Butterfield et al., *Biochem. Biophys. Res. Commun.* 200:710–715 (1994)
Cai et al., *Science* 259:514–516 (1993)
Cashman et al., *Cell* 61:185–192 (1990)
Chartier-Harlin et al., *Nature* 353(6347)844–846 (1991)
Chesebro et al., *Nature* 315:331–333 (1985)
Citron et al., *Proc. Natl. Acad. Sci USA* 91:11993–11997 (1994)
Clements et al. *Neurosci. Lett.* 161:17–20 (1993)
DeArmond et al., *Cell* 41:221–235 (1985)
Dori et al., *Chronobiology* 21:121–126 (1994)
Dyrks et al., *J. Biol. Chem.* 267:18210–18217 (1992)
Fraser et al., *Biophys. J.* 60:1190–1201 (1991)
Fraser et al., *J. Mol. Biol.* 244:64–73 (1994)
Furuta et al., *Am. J. Pathol.* 146:357–367 (1995)
Ghetti et al., *Neurology* 39:1453–1461 (1989)
Glenner et al., *Biochem. Biophys. Res. Commun.* 120:885–890 (1984)
Goate et al., *Nature* 349:704–706 (1991)
Haass et al., *Nature* 359:322–324 (1992)
Harris et al., *Experimental Neurol.* 131:193–202 (1995)
Hendriks et al., *Nat. Genet.* 1:218–221 (1992)
Hensley et al., *Proc. Natl. Acad. Sci. USA* 91(8):3270–3274 (1994)
Hope et al., *EMBO J.* 5:2591–2597 (1986)
Huang et al., *J. Mol. Biol.* 269:214–224 (1997)
Huerto-Delgadillo et al., *J. Pineal Res.* 17:55–62 (1994)
Iguchi et al., *J. Clin. Endocrinol. Metabol.* 55:27–29 (1982)
Jarrett et al., *Biochemistry* 32:4693–4697 (1993)
Johnson-Wood et al., *Proc. Natl. Acad. Sci. USA* 94:1550–1555 (1997)
Kennedy et al., *Brain* 116:309–324 (1993)
Kirchner et al., *Proc. Natl. Acad. Sci. USA* 84:6953–6957 (1987)
Kitamoto et al., *Ann. Neurol.* 20:204–208 (1986)
Kitamoto et al., *Neurology* 41:306–310 (1991)
Kretzschmar et al., *Am. J. Pathol.* 122:1–5 (1986)
Kretzschmar et al., *DNA* 5:315–324 (1986)
Lee et al., *Biochemistry* 34:5191–5200 (1995)
Liao et al., *Science* 233:364–367 (1986)
Ma et al., *Nature* 372:92–94 (1994)
Mattson et al., *Acad. Sci.* 747:50–76 (1994)
McKinley et al., *Cells* 35:57–62 (1982)
Meyer et al., *Proc. Natl. Acad. Sci. USA* 83:2310–2314 (1986)
Mishima et al., *Acta Psychiatr. Scand.* 89:1–7 (1994)
Mullan et al., *Nat. Genet.* 1:325–347 (1992)
Murrell et al., *Science* 254:97–99 (1991)
Neve et al., *Neuron* 1:669–677 (1988)
Nordlund et al., *J. Clin. Endocrinol. Metab.* 45:768–774 (1977)
Oesch et al., *Cell* 40:735–746 (1985)
Pang et al., *Gen. Comp. Endocrinol.* 22:499–506 (1974)
Pappolla et al., *Am. J. Pathol.* 140:621–628 (1992)
Pappolla et al., *Eur. Arch. Psychiatry Clin. Neurosci.* 239:314–319 (1990)
Pappolla et al., *J. Neurosci.* 17:1683–1690 (1997)
Pappolla et al., *Mol. Chem. Neuropathol.* 28:21–34 (1996)
Pappolla et al., *Perspectives in behavioual medicine, Alzheimers disease and AIDS* pp.3–20 (1995)
Perczel et al., *Anal. Biochem.* 203:83–93 (1992)
Pericak-Vance et al., *Am. J. Genet.* 48:1034–1050 (1991)
Perkins et al., *Biological Magnetic Resonance* (1982)
Pierpaoli et al., *Ann. N.Y. Acad. Sci.* 621:291–313 (1991)
Pierpaoli *Aging(Milano)* 3:99–101 (1991)
Prusiner et al., *Cell* 38:127–134 (1984)
Prusiner *Science* 252:1515–22 (1991)
Pucket et al., *Am. J. Hum.* 49:320–329 (1991)
Reiter et al., *Exp. Gerontol.* 30:199–212 (1995)
Reiter et al., *Neuroendocr. Lett.* 15:103–116 (1993)
Robakis et al., *Neurobiol. Aging* 15:A127–129 (1994)
Robakis et al., *Proc. Natl. Acad. Sci. USA* 84:4190–4194 (1987)
Robert et al., *N. Engl. Med.* 315:1231–1233 (1986)
Rumble et al., *N. Engl. J. Med.* 320:1446–1452 (1989)
Sambamurti et al., *J. Neurosci. Res.* 33:319–329 (1992)
Schellenberg et al., *Science* 258:668–671 (1992)
Schellenberg et al., *Ann. Neurol.* 31:223–227 (1992)
Schwarzman et al., *Proc. Natl. Acad. Sci. USA* 91:8368–8372 (1994)
Selkoe, *J. Biol. Chem.* 271:18295 (1996)
Shoji et al., *Science* 258:126–129 (1992)
Skene et al., *Brain Research* 258:126–129 (1992)

Smith et al., *Am. J. Pathol.* 145:42–47 (1994)
Snyder et al., *Biophys. J.* 67:1216–1228 (1994)
Soto et al., *Neurosci. Lett.* 200:105–108 (1995)
Souetre et al., *Am. J. Psychiatry* 146:1037–1040 (1989)
Sparkes et al., *Proc. Natl. Acad. Sci. USA* 83:7358–7362 (1986)
Stahl et al., *Biochemistry* 29:5405–5412 (1990)
Stahl et al., *Cell* 51:229–240 (1987)
Suzuki et al., *Science* 264:1336–1340 (1994)
Tagliavini et al., *EMBO. J.* 10:513–519 (1991)
Tan et al., *Endocrinol. J.* 1:57–60 (1993)
Tanzi et al., *Nature* 331:528–530 (1988)
Tanzi et al., *Am. J. Hum. Genet.* 51:273–282 (1992)
Turk et al., *Eur. J. Biochem.* 176:21–30 (1988)
Van Broeckhoven et al., *Nature* 329:153–155 (1987)
Weidemann et al., *Cell* 57:115–126 (1989)
Wemmer et al., *Nuclear Magnetic Resonance* 239:739–767 (1994)
Wisniewski et al., *Biochem. Biophys. Res. Commun.* 179:1247–1254 (1991)
Wisniewski et al., *Am. J. Pathol.* 145:1030–1035 (1994)
Terzi et al., *J. Mol. Biol.* 252:633–642 (1995)
Yankner et al., *Science* 250:279–282 (1990)
Zagorski et al., *Biochemistry* 31:5621–5631 (1992)
Zhang et al., *Comp. Biochem. Physiol.* 106:165–170 (1993)

What is claimed is:

1. A method for delaying the onset of Alzheimer's Disease in individuals predisposed to Alzheimer's Disease or for treating or delaying the onset of other amyloidosis-related diseases/disorders, comprising administering an effective amount of melatonin to a subject in need thereof to inhibit the formation of fibrils associated with Alzheimer's Disease or to reduce, inhibit or reverse the formation of fibrils or amyloid or amyloid-like deposits associated with amyloidosis-related diseases/disorders other than Alzheimer's Disease.

2. The method for delaying the onset of Alzheimer's Disease according to claim 1, wherein the subject in need thereof is one who is predisposed to Alzheimer's Disease.

3. The method according to claim 2, wherein the subject in need thereof has a genetic predisposition to Alzheimer's Disease.

4. The method for treating or delaying the onset of amyloidosis-related disease/disorder other than Alzheimer's Disease according to claim 1, wherein the subject in need thereof has an amyloidosis-related disease/disorder other than Alzheimer's Disease.

5. The method according to claim 4, wherein the subject in need thereof has a prion-related encephalopathy.

6. The method according to claim 4, wherein the subject in need thereof has senile cardiac amyloidosis.

7. The method according to claim 1, wherein the effective amount of melatonin is administered systemically.

8. The method according to claim 1, wherein the subject in need thereof is human.

9. The method according to claim 1, wherein the effective amount of melatonin is in a range of 20 mg to 1500 mg.

10. The method according to claim 1, wherein the effective amount of melatonin is in a range of 50 to 1500 mg.

11. The method according to claim 1, wherein the effective amount of melatonin is in a range of 50 mg to 500 mg.

12. The method according to claim 1, wherein the effective amount of melatonin is in a range of 100 mg to 500 mg.

* * * * *